(12) United States Patent
Cerri et al.

(10) Patent No.: US 8,822,692 B2
(45) Date of Patent: Sep. 2, 2014

(54) DITERPENOID DERIVATIVES ENDOWED OF BIOLOGICAL PROPERTIES

(71) Applicant: SIGMA-TAU Industrie Farmaceutiche Riunite S.p.A., Rome (IT)

(72) Inventors: Alberto Cerri, Milan (IT); Mauro Gobbini, Mercallo (IT); Marco Torri, Rho (IT); Patrizia Ferrari, Varese (IT); Mara Ferrandi, Milan (IT); Giuseppe Bianchi, Milan (IT)

(73) Assignee: Sigma-Tau Industrie Farmaceutiche Riunite, S.p.A., Rome (IT)

( * ) Notice: Subject to any disclaimer, the term of this patent is extended or adjusted under 35 U.S.C. 154(b) by 0 days.

(21) Appl. No.: 13/951,736

(22) Filed: Jul. 26, 2013

(65) Prior Publication Data

US 2013/0310423 A1 Nov. 21, 2013

Related U.S. Application Data

(63) Continuation of application No. 13/824,556, filed as application No. PCT/EP2011/068702 on Oct. 26, 2011.

(30) Foreign Application Priority Data

Oct. 27, 2010 (EP) .................... 10189058

(51) Int. Cl.

| | |
|---|---|
| *C07D 211/46* | (2006.01) |
| *C07D 207/12* | (2006.01) |
| *C07C 251/58* | (2006.01) |
| *C07C 279/12* | (2006.01) |
| *C07C 277/00* | (2006.01) |
| *C07C 249/04* | (2006.01) |
| *A61K 31/445* | (2006.01) |
| *C07C 217/10* | (2006.01) |
| *C07C 323/25* | (2006.01) |
| *C07C 281/16* | (2006.01) |
| *C07C 251/54* | (2006.01) |
| *C07C 211/31* | (2006.01) |
| *C07C 251/60* | (2006.01) |

(52) U.S. Cl.
CPC ........... *C07C 251/58* (2013.01); *C07C 2103/26* (2013.01); *C07C 217/10* (2013.01); *C07C 323/25* (2013.01); *C07C 277/00* (2013.01); *C07C 279/12* (2013.01); *C07D 211/46* (2013.01); *C07C 281/16* (2013.01); *C07D 207/12* (2013.01); *C07C 251/54* (2013.01); *C07B 2200/07* (2013.01); *C07C 249/04* (2013.01); *C07C 211/31* (2013.01); *C07C 251/60* (2013.01)
USPC ........... 546/204; 514/325; 514/424; 514/548; 546/203; 560/194; 548/528

(58) Field of Classification Search
USPC .......................................... 514/235; 546/204
See application file for complete search history.

(56) References Cited

U.S. PATENT DOCUMENTS

| | | |
|---|---|---|
| 2004/0116482 A1 | 6/2004 | Imaizumi et al. |
| 2006/0148904 A1 | 7/2006 | Protopopova et al. |
| 2006/0235072 A1 | 10/2006 | Imaizumi et al. |

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*
Wada; Chem. Pharm. Bull. 1985, 33, 1472-1487.*
Wermuth; Practice of Medicinal Chemistry, 2003, second edition, Academic Press, Chapter 12, pp. 175-188.*
San Feliciano, Planta Med., 1993, 59, 485-490.*
von Rudolf Albrecht, et al., Darstellung Von Analogen Des Dehydroabietylamins . . . , Liebigs Ann. Chem., vol. 725, pp. 154-166, 1969.
Constantin Czekelius, et al., Convenient Transformation of Optically . . . , Angew. Chem. Int. Ed., vol. 44, pp. 612-615, 2005.
H. Hoffmann-La Roche AG, et al., 64, Stereoselective Partial Synthesis . . . , Helvetica Chimica Acta, vol. 78, 1995, XP-002630678.

* cited by examiner

*Primary Examiner* — John Mabry
*Assistant Examiner* — Daniel Carcanague
(74) *Attorney, Agent, or Firm* — Lucas & Mercanti, LLP

(57) ABSTRACT

The present invention relates to new diterpenoid derivatives of formula (I), processes for their preparation, and to pharmaceutical compositions containing them for the treatment of cardiovascular disorders, urinary incontinence, asthma, or Alzheimer's disease and/or to prevent obstructive vascular lesions consequently to arteriotomy and/or angioplasty, and to prevent organ damage in hypertensive patients.

8 Claims, No Drawings

DITERPENOID DERIVATIVES ENDOWED OF BIOLOGICAL PROPERTIES

This application is a continuation of U.S. Ser. No. 13/824,556 filed on Mar. 18, 2013, which is a U.S. national stage of PCT/EP2011/068702 filed on Oct. 26, 2011, which claims priority to and the benefit of European Application No. 10189058.0, filed on Oct. 27, 2010, the contents of each of which are incorporated herein by reference in their entirety.

The present invention relates to new diterpenoid derivatives, process for their preparation, and to pharmaceutical compositions containing them for the prevention and/or treatment of cardiovascular disorders, obstructive vascular lesions consequently to arteriotomy and/or angioplasty, and to prevent organ damage in hypertensive patients.

BACKGROUND OF THE INVENTION

The compounds of the present invention belong to the class of the diterpenoid derivatives and have demonstrated to possess cardiovascular properties which render them useful for the prevention and/or treatment of hypertension, heart failure, cardiac hypertrophy, renal failure, glomerulosclerosis, proteinuria, vascular stenosis after vascular surgery and to prevent organ damage in hypertensive patients.

Cardiovascular diseases are still the first cause of morbidity and mortality in the western world; among these, hypertension and heart failure are two frequent diseases. Hypertension is one of the most important cardiovascular risk factor and more than one third of the population over 60 suffers from this disease. Congestive heart failure affects 1-2% of the population and even 10% of the very elderly; the percentage is expected to rise (Sharpe N., et al., *The Lancet*, 1998, 352, (suppl. 1), 3-17). Beside, hypertension may be one of the most important causes of heart failure in the elderly (Remme W. J., et al., *Eur. Heart J.*, 2001, 22, 1527-1560). Although a number of effective drugs are available for the treatment of both hypertension and heart failure, further research is in progress to find more effective and safer compounds. Several drugs are used in combination for the treatment of heart failure, and among positive inotropic agents, digoxin is the most prescribed digitalis cardiac glycoside that can improve the myocardial performance. However, a very well known drawback of digitalis drugs is their arrhythmogenic side effect. Evidence of digitalis toxicity such as disturbances of conduction and cardiac arrhythmias which are characteristics of digitalis toxicity (Hoffman, B. F., et al., Digitalis and Allied Cardiac Glycosides; *The Pharmacological Basis of Therapeutics*, 8th ed.; Goodman Gilman A.; Nies A. S., Rall T. W., Taylor P., Eds.; Pergamon Press, New York, 1990, 814-839) emerges at two- to three-fold higher serum concentration than the therapeutic dose.

The present compounds are useful for the prevention and/or treatment of cardiovascular disorders. Indeed, said compounds are able to antagonize the effects of mutant α-adducin and ouabain which are both known to be implicated in human hypertension and related organ complications and cardiac hypertrophy and/or failure.

Furthermore, the instant compounds do not inhibit the Na-K ATPase pump and therefore do not present the safety issue (e.g., arrhythmogenic side-effects) associated to such inhibition.

Endogenous ouabain (EO) has been widely recognized as a new hormone able to control blood pressure through different mechanisms and in particular through the modulation of the renal Na handling. Moreover, high circulating levels of EO have been found to be associated with cardiac and renal hypertrophy in animal models such as the Ouabain Hypertensive Rats model (OHR) (Ferrandi M., et al., *J. Biol. Chem.*, 2004, 279, 32, 33306) and with cardiac and renal dysfunctions in humans (Pierdomenico S. D., et al., *Am. J. Hypertens.*, 2001, 14, 1, 44; Stella P., et al., *J. Int. Med.*, 2008, 263, 274).

Mutations in the genes coding for the cytoskeletal protein adducin were found to be associated to hypertension and related organ complications (Bianchi G., et al., *Hypertension*, 2005, 45, 3, 331). In particular, adducin is involved in many cellular processes, some of which being affected by the mutations and having relevance in hypertension and related organ complications such as:

i. the regulation of the residential time of some integral proteins on the cell surface (Na-KATPase, integrin) (Efendiev R., et al., Circ. Res., 2004, 95, 11, 1100; Torielli L., et al., *Am. J. Renal Physiol.*, 2008, 295, 2, F478);

ii. the influence on the constitutive $Na^+$ reabsorption capacity of the renal tubular cell (Bianchi G., et al., *Hypertension*, 2005, 45, 3, 331);

iii. the regulation of the expression of some glomerular podocyte proteins (nephron, synaptopodin) associated to proteinuria and progression of renal damage both in animal models and humans (Ferrandi M., et al., *J. Mol. Med.*, 2010, 88, 203).

Experimental evidence obtained both in the Milan hypertensive rat model (MHS) and in humans supports the role of adducin polymorphisms in hypertension and related organ complication, including deterioration of the renal function and proteinuria (Citterio L., et al., *Biochim. Biophys. Acta*, 2010, Apr. 8).

Both EO and mutant adducin can lead to hypertension, organ hypertrophy, renal failure, proteinuria, negative vascular remodeling and increased cardiovascular risk through the up-regulation of the Na-K pump, activation of the Src-dependent signal transduction pathway or other pathways modulating actin cytoskeleton.

The abietic acid and dehydroabietic acid derivatives object of the present invention have been found to be endowed of suitable cardiovascular pharmacological properties, and/or able to prevent organ damage, and/or prevent proteinuria. In particular, the abietic acid or dehydroabietic acid derivatives object of the present invention have been found to antagonize the effects of EO and mutant adducin on blood pressure and renal function deterioration and proteinuria.

A further important biological activity of the present compounds resides in their ability to reduce proteinuria induced by endogenous ouabain and to prevent organ damage.

Some dehydroabietic acid derivatives have been described as being endowed of anti-ulcer properties (Wada H., et al., *Chem. Pharm. Bull.*, 1985, 33, 4).

WO2005084141 disclosed the specific dehydroabietane derivative 1 as being endowed of said properties through acyl-CoA:cholesterol acyltransferase inhibition properties.

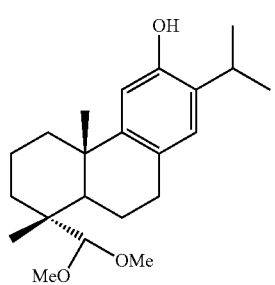

1

EP1421936 (i.e., the European national phase, now refused, of WO2002087559) disclosed potassium channel opener derivatives of formula 2. However, only three derivatives structurally different to the compounds of the preterit invention were specifically reported among. The inventors of this patent application also published further data regarding said compounds of formula 2 acknowledging the fact that abietic derivatives were not active on large-conductance K⁻ channels contrarily to the pimaric acid derivatives disclosed despite only very small differences in their chemical structures.

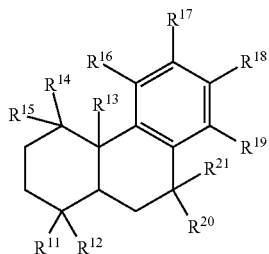

2

WO10024298 disclosed potassium channel modulator derivatives of formula 3 which are structurally different to the compounds of the present invention.

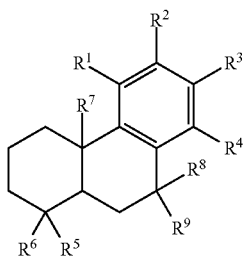

3

The preparation of very few antiarrhythmic compounds derived from esterification of abietic acid have also been reported some forty years ago (Sefcovic P., et al., Chemicke Zvesti, 1961, 15, 554); however, the compounds of the present invention were not disclosed nor suggested.

An enantioselective and catalytic synthesis of an oxime abietic derivative has been disclosed starting from the corresponding enantic pure nitro analogue (Czekelius C., et al., Angew. Chem. Int. Ed., 2005, 44, 612).

More than forty years ago, synthesis of dehydroabietic derivatives had been described, the latter being motivated for the known antibacterial properties of those scaffold-containing adducts (von Rudolf A., et al., Liebigs Ann. Chem., 1969, 725, 154).

Nevertheless, as the literature demonstrates, the need of new derivatives endowed with suitable cardiovascular pharmacological properties, and/or able to prevent organ damage, and/or prevent proteinuria still persists.

DESCRIPTION OF THE INVENTION

The present invention relates to new abietic acid and dehydroabietic acid derivatives of formula (I), or a salt, hydrate or solvate thereof, in the preparation of a composition for the prevention and/or treatment of hypertension, heart failure, cardiac hypertrophy, renal failure, glomerulosclerosis, proteinuria, vascular stenosis after vascular surgery and to prevent organ damage in hypertensive patients:

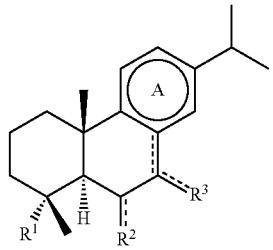

I wherein:
$R^1$ is —CH=NOR⁴ with the meaning of iminoxy, —CH₂NHOR⁴, —CH₂XR⁵, —CH=CHR⁶, —CH=NR⁷, amino-($C_3$-$C_6$)alky or heterocycloalkyl-alkyl wherein the heterocycloalkyl moiety is selected from the group consisting of piperidinyl, pyrrolidinyl and tetrahydrofuranyl;

$R^7$ is guanidino;

$R^6$ is amino-($C_1$-$C_6$)alkyl or heterocycloalkyl-alkyl wherein the heterocycloalkyl moiety is selected from the group consisting of piperidinyl, pyrroiidinyl and tetrahydrofuranyl;

$R^5$ is amino-($C_1$-$C_6$)alkyl or heterocycloalkyl-alkyl wherein the heterocycloalkyl moiety is selected from the group consisting of piperidinyl, pyrroiidinyl and tetrahydrofuranyl;

$R^4$ is H, amino-($C_1$-$C_6$)alkyl, heterocycloalkyl, hydroxyalkyl, hydroxyalkyloxyalkyl, or carboxyalkyl;

X is O or S;

the endocyclic symbol ⚌ represents a single or a double bond and when it represents a double bond the symbol ⚌ linking $R^3$ to the carbocycle represents a single bond and the carbocycle ring A is partially unsaturated;

the symbol ⚌ linking $R^2$ to the carbocycle represents a single or a double bond;

$R^2$ is H or hydroxyl when the symbol ⚌ linking $R^2$ to the carbocycle represents a single bond; or $R^2$ is O or N~OR⁸ when the symbol ⚌ linking $R^2$ to the carbocycle represents a double bond with the meaning of carbonyl or oxime respectively;

$R^8$ is H or ($C_1$-$C_6$)alkyl;

the symbol ⚌ linking $R^3$ to the carbocycle represents a single or a double bond;

$R^3$ is H when the symbol ⚌ linking $R^3$ to the carbocycle represents a single bond; or $R^3$ is O or N~OR⁸ when the symbol ⚌ linking $R^3$ to the carbocycle represents a double bond with the meaning of carbonyl or oxime respectively;

carbocycle ring A is aromatic or partially unsaturated;

with the proviso that when $R^4$ is H, $R^2$ is not H;

their optically active forms such as enantiomers, diastereomers, their racemate forms, and pharmaceutically acceptable salts thereof.

An embodiment of this invention is that of compounds of formula I, for use as medicaments.

In a further embodiment, said medicament is used for the prevention and/or treatment of cardiovascular disorders, obstructive vascular lesions consequently to arteriotomy and/or angioplasty, and to prevent organ damage in hypertensive patients.

In a preferred embodiment, said medicament is used for preventing and/or treating hypertension, heart failure or to prevent organ damage in hypertensive patients.

The term "alkyl" unless otherwise specified, refers to linear or branched alkyl groups having from 1 to 20 carbon atoms, or preferably, 1 to 12 carbon atoms or even more preferably 1 to about 6 carbon atoms.

The term "amino" refers to the group —$NH_2$.

The term "amino-($C_1$-$C_6$)alkyl" refers to the group alkyl having up to six carbon atoms as defined above winch is substituted by an amino group as defined above.

The term "heterocycloalkyl" refers to a saturated or partially unsaturated (but not aromatic) five-, six- or seven-membered ring containing one or more nitrogen, oxygen or sulfur atoms which may be the same or different and which rings may be substituted with lower alkyl, lower alkenyl or aryl. Preferred heterocycloalkyl include pyrrolidine, piperidine, piperazine, ketopiperazine, 2,5-diketopiperazine, morpholine, thiomorpholine, dihydropyranyl, tetrahydropyranyl, tetrahydrofurane, dihydropyrrole, imidazolidine, dihydropyrazole, pyrazolidine and the like. Even more preferred heterocycloalkyl are pyrrolidine, piperidine, piperazine and morpholine.

The term "hydroxyalkyl" refers to the group alkyl as defined above which is substituted by a hydroxyl group.

The term "alkyloxy" refers to the group —O—R where R includes "($C_1$-$C_6$)alkyl", "($C_3$-$C_{10}$)cycloalkyl" and "heterocycloalkyl".

The term "alkyloxyalkyl" refers to the group alkyl as defined above which is substituted by an alkyloxy group as above defined.

The term "hydroxyalkyloxy alkyl" refers to the group alkyloxyalkyl as defined above which is substituted by a hydroxyl group.

The term "carboxyalkyl" refers to alkyl groups as defined above having a carboxy substituent. Preferred carboxyalkyl are groups where the alkyl radical contains from 1 to 6 carbon atoms, including 2-carboxymethyl, 2-carboxyethyl and the like. The expression "pharmaceutically acceptable salts" refers to salts of the below identified compounds of formulae (I), that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, toluene sulfonic acid, naphthalene disulfonic acid, methanesulfonic acid and poly-galacturonic acid. When the salt is of a mono acid (for example, the hydrochloride, the hydrobromide, the p-toluenesulphonate, or the acetate), at least one molar equivalent and usually a molar excess of the acid is employed. However, when such salts as the sulphate, the hemisuccinate, the hydrogen phosphate, or the phosphate are desired, the appropriate and exact chemical equivalents of acid are generally used. Suitable pharmaceutically acceptable base addition salts tor the compound of the present invention include metallic salts made from aluminium, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Sodium salts are particularly preferred.

The invention furthermore provides a process for the preparation of compounds of formula I, which can be obtained as detailed underneath.

Compounds of general formula (I) wherein the symbol $R^1$ is —CH=$NOR^4$ with the meaning of iminoxy; carbocycle ring A is aromatic or partially unsaturated and $R^2$ and $R^3$ are as defined above, can be obtained for example by reacting a compound of Formula II,

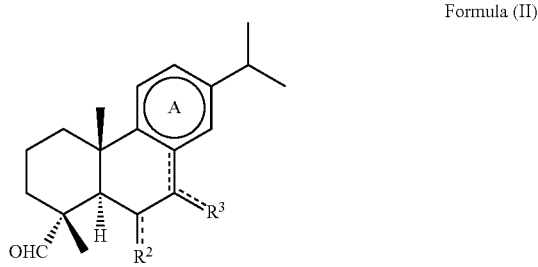

Formula (II)

wherein carbocycle ring A is aromatic or partially unsaturated and $R^2$ and $R^3$ are as defined above, with a compound of formula (III)

$R^4ONH_2.xHCl$ (formula III)

wherein $R^4$ is as defined above, and x is an integer comprised between 0 and 3; in pyridine at room temperature.

Alternatively, compounds of general formula (I) wherein the symbol $R^1$ is —CH=$NOR^4$ with the meaning of iminoxy; carbocycle ring A is aromatic or partially unsaturated $R^2$ and $R^3$ are as defined above, can be obtained for example by reacting a compound of Formula (II) as defined above with a compound of Formula (III) as defined above, in an aprotic solvent such as tetrahydrofuran in the presence of $Na_2HPO_4.12H_2O$.

In all said transformations, any interfering reactive group can be protected and then deprotected according to well-established procedures described in organic chemistry (see for example: Greene T. W. and P. G. M. Wuts "Protective Groups in Organic Synthesis", J. Wiley & Sons, Inc., $3^{rd}$ Ed., 1999) and well known to those skilled in the art.

All said transformations are only examples of well-established procedures described in organic chemistry (see for example: J. March "Advanced Organic Chemistry", J. Wiley & Sons, Inc., $4^{th}$ Ed., 1992) and well known to those skilled in the art.

We have found that the derivatives (I) and their pharmaceutically acceptable salts, prepared according to the invention, are useful agents for the prevention and/or treatment of cardiovascular disorders, obstructive vascular lesions consequently to arteriotomy and/or angioplasty, and to prevent organ damage in hypertensive patients.

Therefore another object of the present invention is a method of treating a mammal suffering from cardiovascular disorders, obstructive vascular lesions consequently to arteriotomy and/or angioplasty, comprising administering a therapeutically effective amount of a compound of Formula (I) as described above. The term "therapeutically effective amount" as used herein refers to an amount of a therapeutic agent needed to treat, ameliorate a targeted disease or condition, or to exhibit a detectable therapeutic effect.

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in *Remington's Pharmaceuti-* cal Science Handbook, Mack Pub, N.Y.—last edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

For any compound, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information, can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.001 mg/kg to 10 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of the therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing.

The expression "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Dosage treatment may be a single dose schedule or a multiple dose schedule.

A further object of the present invention is the use of said compounds of general formula (I) in the preparation of a medicament useful in the treatment of cardiovascular diseases such as heart failure and hypertension. Hypertension affects approximately 30% of the world's population and represents the leading preventable cause of premature morbidity and mortality due to major cardiovascular events and organ cardiovascular complications such as coronary heart disease, chronic heart failure, stroke, kidney failure, negative vascular remodelling, retinal damage and cognitive disorders (Ritz E., Am. J. Cardiol., 2007, 100(3A), 53J-60J; Messerli F. H., et al., Lancet, 2007, 370, 9587, 591).

A further object of the present invention are pharmaceutical compositions containing one or more of the compounds of formula (I) described earlier, in combination with excipients and/or pharmacologically acceptable diluents.

The compositions in question may, together with the compounds of formula (I), contain known active principles.

A further embodiment of the invention is a process for the preparation of pharmaceutical compositions characterised by mixing one or more compounds of formula (I) with suitable excipients, stabilizers and/or pharmaceutically acceptable diluents.

A still further embodiment of this invention is that of compounds of formula (I) described earlier, wherein $R^1$ represents is —CH=NOR$^4$ wherein $R^4$ is amino-$(C_1-C_6)$alkyl or heterocycloalkyl.

The following illustrated Examples are by no means an exhaustive list of what the present invention intends to protect.

EXAMPLES

Abbreviations

AcOEt: ethyl acetate
AcOH: acetic acid
9-BBN: 9-borabicyclo[3.3.1]nonane
DCM: dichloromethane
DIAD: diisopropyl azodicarboxylate
DMSO: dimethylsyulfoxide
Et$_2$O: diethyl ether
EtOH: ethanol
HMPA: hexamethylphosphoramide
H$_2$O$_2$: hydrogen peroxide
H$_2$SO$_4$: sulphuric acid
IBX: 2-iodoxybenzoic acid
KOtBu: potassium terbutoxide
MeOH: methanol
NaBH$_3$CN: sodium cyanoborohydride
NaH: sodium hydride
NaHCO$_3$: sodium bicarbonate
NaH$_2$PO$_4$: sodium phosphate
NaOH: sodium hydroxide Na₂SO₄: sodium sulphate
Na₂S₂O₃: sodium thiosulphate
NH₄OH: ammonium hydroxide
PTSA: para-toluene sulfonic acid
RT: room temperature
THF: tetrahydrofurane General Remarks Flash column chromatography was carried out using silica gel (Merck 230-400 mesh). Mass spectral data were obtained with electron impact ionization technique at 70 eV from a Finnigan INCOS-50 mass spectrometer using the direct exposure probe.

Example 1

(E)-15-(2)-Aminoethoxyimino)-13-isopropylpodocarpa-8,11,13-triene fumarate

A solution of 76 mg of 13-isopropylpodocarpa-8,11,13-triene-15-aldehyde (González M. A.; et al., *Eur. J. Med. Chem.*, 2010, 45, 811), 33 mg of 2-aminoethoxyamine dihydrochloride in 1 ml of pyridine was stirred at RT for 1 hour. Pyridine was evaporated and the crude reaction mixture was purified by flash chromatography using DCM/MeOH/NE₄OH 95/5/0.5 as eluent. The solvent was removed under vacuum and the residue was dissolved in MeOH. A stoichiometric amount of fumaric acid was added and the solution evaporated to dryness under vacuum. The title compound was obtained as a white solid.

Yield: 35% (43 mg).
¹H-NMR (300 MHz, DMSO-d₆) δ: 8.70 (bb, 4H), 7.28 (s, 1H), 7.15 (d, 1H), 6.95 (dd, 1H), 6.83 (d, 1H), 6.41 (s, 2H), 4.05 (t, 2H), 2.97 (t, 2H), 2.77 (m, 3H), 2.29 (m, 1H), 1.80-1.20 (m, 8H), 1.14 (s, 3H), 1.13 (d, 6H), 1.10 (s, 3H).
MS: 342 (M⁺).

Examples 2-8 were synthesized following the experimental conditions described in example 1, using the relevant amine instead of 2-aminoethoxyamine dihydrochloride. The salification step was omitted for compounds that did not present any basic amino group on the side chain.

Example 2

(E)-15-(3-Aminopropoxyimino)-13-isopropylpodocarpa-8,11,13-triene fumarate

Yield: 64% (77 mg),
¹H-NMR (300 MHz, DMSO-d₆) δ: 8.80 (bb, 4H), 7.24 (s, 1H), 7.15 (d, 1H), 6.95 (dd, 1H), 6.83 (d, 1H), 6.39 (s, 2H), 3.99 (t, 2H), 2.78 (m, 5H), 2.28 (m, 1H), 1.84 (m, 2H), 1.80-1.20 (m, 8H), 1.14 (d, 3H), 1.13 (s, 3H), 1.09 (s, 3H).
MS: 356 (M⁺).

Example 3

(E)-15-(4-Aminobutoxyimino)-13-isopropylpodocarpa-8,11,13-triene fumarate

The title compound was obtained by simply triturating it in a mixture of AcOEt/Et₂O, after salt formation.
Yield: 49% (100 mg).
¹H-NMR (300 MHz, DMSO-d₆) δ: 8.75 (bb, 4H), 7.21 (s, 1H), 7.15 (d, 1H), 6.96 (dd, 1H), 6.83 (d, 1H), 6.38 (s, 2H), 3.94 (t, 2H), 2.76 (m, 5H), 2.29 (m, 1H), 1.85-1.20 (m, 12H), 1.14 (d, 6H), 1.14 (s, 3H), 1.09 (s, 3H).
MS: 370 (M⁺).

Example 4

(E)-15-((R)-3-Pyrrolidinyloxyimino)-13-isopropylpodocarpa-8,11,13-triene fumarate The title compound was obtained by simply triturating it in Et₂O, after salt formation.
Yield: 80% (5.10 g).
¹H-NMR (300 MHz, DMSO-d₆) δ: 9.05 (bb, 3H), 7.24 (s, 1H), 7.15 (d, 1H), 6.95 (dd, 1H), 6.83 (d, 1H), 6.40 (s, 2H), 4.73 (m, 1H), 3.20-2.95 (m, 4H), 2.75 (m, 3H), 2.29 (m, 1H), 1.98 (m, 2H), 1.85-1.20 (m, 8H), 1.14 (d, 6H), 1.14 (s, 3H), 1.10 (s, 3H).
MS: 368 (M⁺).

Example 5

(E)-15-((S)-3-Pyrrolidinyloxyimino)-13-isopropylpodocarpa-8,11,13-triene fumarate The title compound was obtained by simply triturating it in Et₂O, after salt formation.
Yield: 72% (243 mg).
¹H-NMR (300 MHz, DMSO-d₆ and TFA) δ: 8.94 (bb, 1H), 8.84 (bb, 1H), 7.27 (s, 1H), 7.15 (d, 1H), 6.95 (dd, 1H), 6.83 (d, 1H), 6.62 (s, 2H), 4.78 (m, 1H), 3.31 (m, 2H), 3.20 (m, 2H), 2.76 (m, 3H), 2.29 (m, 1H), 2.08 (m, 2H), 1.80-1.20 (m, 8H), 1.15-1.10 (m, 12H),
MS: 368 (M⁺).

Example 6

(E)-15-(4-Piperidinyloxyimino)-13-isopropylpodocarpa-8,11,13-triene fumarate

The title compound was obtained by simply triturating it in Et₂O, after salt formation.
Yield: 90% (185 mg).
¹H-NMR (300 MHz, DMSO-d₆ and TFA) δ: 8.45 (bb, 1H), 8.34 (bb, 1H), 7.27 (s, 1H), 7.15 (d, 1H), 6.95 (dd, 1H), 6.82 (d, 1H), 6.61 (s, 2H), 4.19 (m, 1H), 3.25-2.65 (m, 7H), 2.28 (m, 1H), 2.07-1.20 (m, 12H), 1.14 (s, 3H), 1.13 (d, 6H), 1.09 (s, 3H).
MS: 382 (M⁺).

Example 7

(E)-15-(3-Hydroxypropoxyimino)-13-isopropylpodocarpa-8,11,13-triene

The flash chromatography purification was done by means of n-hexane/AcOEt 75:25 as the eluent.
Yield: 52% (130 mg).
¹H-NMR (300 MHz, DMSO-d₆) δ: 7.20 (s, 1H), 7.15 (d, 1H), 6.95 (dd, 1H), 6.83 (d, 1H), 4.43 (t, 1H), 3.97 (t, 2H), 3.44 (dt, 2H), 2.77 (m, 3H), 2.28 (m, 1H), 1.80-1.20 (m, 10H), 1.14 (s, 3H), 1.14 (d, 6H), 1.09 (s, 3H).
MS: 357 (M⁺).

Example 8

(E)-15-(3-(3-Hydroxypropoxy)propoxyimino)-13-isopropylpodocarpa-8,11,13-triene

The flash chromatography purification was conducted as exemplified in example 7.
Yield: 14% (40 mg).
¹H-NMR (300 MHz, DMSO-d₆) δ: 7.21 (s, 1H), 7.15 (d, 1H), 6.95 (dd, 1H), 6.83 (d, 1H), 4.36 (t, 1H), 3.96 (t, 2H), 3.41 (m, 6H), 2.77 (m, 3H), 2.28 (m, 1H), 1.85-1.20 (m, 12H), 1.14 (s, 3H), 1.14 (d, 6H), 1.09 (s, 3H).
MS: 415 (M⁺).

Example 9

(E)-15-Guanidinoimino-13-isopropylpodocarpa-8,11,13-triene

A solution of 80 mg of aminoguanidine hydrochloride in 0.8 ml of 1N HCl was added to a solution 200 mg of 13-isopropylpodocarpa-8,11,13-triene-15-aldehyde in 1 ml of dioxane. The mixture was heated to 80° C. for 5 hours. After cooling, the solvent was removed under reduced pressure and the crude reaction mixture was purified by flash chromatography using DCM/MeOH/NH$_4$OH 90/10/1 as eluent.

The pure fractions were evaporated to dryness. The title compound was obtained as a white solid.

Yield: 92% (221 mg).

$^1$H-NMR (300 MHz, DMSO-d$_6$) δ: 7.15 (d, 1H), 7.09 (s, 1H), 6.95 (dd, 1H), 6.83 (d, 1H), 5.50 (bb, 2H), 5.16 (bb, 2H), 2.76 (m, 3H), 2.28 (m, 1H), 1.80-1.20 (m, 8H), 1.15 (s, 3H) 1.14 (d, 6H), 1.11 (s, 3H).

MS: 340 (M$^+$).

Example 10

(E)-15-Carboxymethoxyimino-13-isopropylpodocarpa-8,11,13-triene

A solution of 160 mg of 2-aminooxyacetic acid in 2 ml of H$_2$O was added to a solution 200 mg of 13-isopropylpodocarpa-8,11,13-triene-15-aldehyde in 5 ml of THF. After stirring at RT for 4 hours, the solvent was removed under reduced pressure and the crude reaction mixture was purified by flash chromatography using DCM/MeOH 9:1 as eluent. The title compound was obtained as a white solid.

Yield: 91% (230 mg).

$^1$H-NMR (300 MHz, DMSO-d$_6$) δ: 12.64 (bb, 1H), 7.31 (s, 1H), 7.15 (d, 1H), 6.95 (dd, 1H), 6.84 (d, 1H), 4.44 (s, 2H), 2.76 (m, 3H), 2.28 (m, 1H), 1.80-1.20 (m, 8H), 1.14 (d, 6H), 1.13 (s, 3H), 1.07 (s, 3H).

MS: 357 (M$^+$).

Example 11

(E)-15-(2-Aminoethoxyimino)-13-isopropylpodocarpa-8,11,13-triene-6-one fumarate Step A: Methyl 7-oxo-13-isopropylpodocarpa-8,11,13-triene-15-carboxylate A solution of 5.72 g of CrO$_3$ in 100 ml of AcOH/H$_2$O 4:1 was added at 10° C. over a 15 minutes period and under vigorous stirring, to a solution of 5.00 g of methyl 13-isopropylpodocarpa-8,11,13-triene-15-carboxylate (González M. A., et al., *Eur. J. Med. Chem.*, 2010, 45, 811) in 80 ml of AcOH. The reaction mixture was then cooled to 4° C. and stirred for 2 days before being poured into 500 ml of H$_2$O and extracted several times with Et$_2$O. The combined organic extracts were washed with H$_2$O, 5% aq.NaHCO$_3$ until neutral pH was reached, and brine. The organic phase was dried over Na$_2$SO$_4$ and the solvent was removed under reduced pressure. The residue was purified by flash chromatography using cyclohexane/AcOEt 95/5 to afford the desired adduct.

Yield: 58% (3.05 g).

$^1$H-NMR (300 MHz, DMSO-d$_6$) δ: 7.68 (d, 1H), 7.50 (dd, 1H), 7.40 (d, 1H), 3.59 (s, 3H), 2.90 (m, 1H), 2.80 (dd, 1H), 2.48 (dd, 1H), 2.38 (m, 1H), 2.09 (dd, 1H), 1.75-1.40 (m, 5H), 1.26 (s, 3H), 1.20 (s, 3H), 1.18 (d, 6H).

MS: 328 (M$^+$).

Step B: Methyl 7-acetoxy-13-isopropylpodocarpa-6,8,11,13-tetraene-15-carboxylate A solution of 4.30 g of methyl 7-oxo-13-isopropylpodocarpa-8,11,13-triene-15-carboxylate and 0.25 mg of PTSA in 51 ml of isopropenyl acetate was refluxed for 3 days. Alter cooling, the solution was washed with 5% aqueous NaHCO$_3$ (3×20 ml), and brine. After drying over Na$_2$SO$_4$, the solution was concentrated under reduced pressure. The resulting residue was purified by flash chromatography using n-hexane/AcOEt 93/7 to give the desired adduct.

Yield: 74% (3.50 g).

$^1$H-NMR (300 MHz, DMSO-d$_6$) δ: 7.17 (dd, 1H), 7.13 (d, 1H), 6.90 (d, 1H), 5.34 (d, 1H), 3.58 (s, 3H), 2.85 (m, 1H), 2.80 (d, 1H), 2.27 (s, 3H), 2.17 (m, 1H) 1.80-1.50 (m, 5H), 1.31 (s, 3H), 1.16 (d, 3H), 1.15 (d, 3H), 1.10 (s, 3H).

MS: 370 (M$^+$)

Step C: 6α-hydroxy-7-oxo-13-isopropylpodocarpa-8,11,13-triene-15-carboxylate 12.1 ml of peracetic acid were added dropwise at 0° C. to a solution of 3.55 g of methyl 7-acetoxy-13-isopropylpodocarpa-6,8,11,13-tetraene-15-carboxylate in 50 ml of CHCl$_3$. After 24 hours at RT the reaction mixture was cooled to 0° C. and a 10% aqueous NaI solution was added until a brown colour appeared. Ten minutes after, a saturated aqueous solution of Na$_2$S$_2$O$_3$ was added until disappearance of the brown colour. The phases were separated and the aqueous layer was extracted with CHCl$_3$ (3×50 ml). The combined organic phases were dried over Na$_2$SO$_4$ and evaporated to dryness to give a 3/2 mixture of methyl 6α-acetoxy-7-oxo-13-isopropylpodocarpa-8,11,13-triene-15-carboxylate and methyl 6α-hydroxy-7-oxo-13-isopropylpodocarpa-8,11,13-triene-15-carboxylate.

Yield: 93% (3.44 g).

Methyl 6α-acetoxy-7-oxo-13-isopropylpodocarpa-8,11,13-triene-15-carboxylate $^1$H-NMR (300 MHz, DMSO-d$_6$) δ: 7.72 (d, 1H), 7.58 (dd, 1H), 7.48 (d, 1H), 5.40 (d, 1H), 3.59 (s, 3H), 2.96 (d, 1H), 2.94 (m, 1H), 2.46 (m, 1H), 2.02 (s, 3H), 1.80-1.40 (m, 5H), 1.34 (s, 3H), 1.22 (s, 3H), 1.19 (d, 6H).

MS: 386 (M$^+$).

Methyl 6α-hydroxy-7-oxo-13-isopropylpodocarpa-8,11,13-triene-15-carboxylate $^1$H-NMR (309 MHz, DMSO-d$_6$) δ: 7.73 (d, 1H), 7.51 (dd, 1H), 7.42 (d, 1H), 5.33 (d, 1H), 4.37 (dd, 1H), 3.46 (s, 3H), 2.94 (m, 1H), 2.70 (d, 1H), 2.38 (m, 1H), 1.80-1.33 (m, 5H), 1.36 (s, 3H), 1.27 (s, 3H), 1.19 (d, 6H).

MS: 344 (M$^+$).

Step D: 13-isopropylpodocarpa-8,11,13-trine-6α,15-diol 3 drops of concentrated H$_2$SO$_4$ followed by 0.16 g of 10% Pd/C were added to a solution of 0.83 g of a 3/2 mixture of methyl 6α-acetoxy-7-oxo-13-isopropylpodocarpa-8,11,13-triene-15-carboxylate and methyl 6α-hydroxy-7-oxo-13-isopropylpodocarpa-8,11,13-triaene-15-carboxylate in 15 ml of AcOH. The mixture was hydrogenated at RT at 50 psi for 3 hours. The reaction, mixture was filtered. The resulting solution was diluted with Et$_2$O and neutralized by addition of 5% aqueous NaHCO$_3$. The layers were separated and the aqueous one was extracted with Et$_2$O. The combined organic phases were washed with 5% aqueous NaHCO$_3$, brine, dried over Na$_2$SO$_4$ and evaporated. The residue was purified by flash chromatography using n-hexane/AcOEt 9/1 to give a 7/3 mixture of methyl 6α-acetoxy-13-isopropylpodocarpa-8,11,13-triene-15-carboxylate and 6α-hydroxy-13-isopropylpodocarpa-8,11,13-triene-15-carboxylic acid lactone.

Yield: 68% (0.54 g).

Methyl 6α-acetoxy-13-isopropylpodocarpa-8,11,13-triene-15-carboxylate

¹H-NMR (300 MHz, Acetone-d₆) δ: 7.21 (d, 1H), 7.05 (dd, 1H), 6.93 (d, 1H), 5.30 (m, 1H), 3.66 (s, 3H), 3.36 (dd, 1H), 2.90-2.60 (m, 3H), 2.38 (m, 1H), 1.95 (s, 3H), 1.80-1.50 (m, 5H), 1.24 (s, 3H), 1.23 (s, 3H), 1.20 (d, 6H).

MS: 372 (M⁺).

6α-Hydroxy-13-isopropylpodocarpa-8,11,13-triene-15-carboxylic acid lactone

¹H-NMR (300 MHz, Acetone-d₆) δ: 7.21 (d, 1H), 7.10 (dd, 1H), 7.01 (d, 1H), 4.80 (m, 1H), 3.44 (dd, 1H), 2.95-2.75 (m, 3H), 2.23 (m, 1H), 1.85-1.40 (m, 5H), 1.20 (s, 3H), 1.25 (s, 3H), 1.21 (d, 6H).

MS: 298 (M⁺).

The above mixture was added into a suspension of 540 mg of LiAlH₄ in 15 ml of dry THF at 0° C. The reaction mixture was heated to reflux for 1 hour and then cooled to 0° C. The reaction mixture was quenched by addition of 0.54 ml of H₂O, 0.54 ml of 30% NaOH and 1.65 ml of H₂O. After warming to RT, the reaction mixture was littered and the resulting filtrate rinsed with AcOEt and DCM. The organic layer was concentrated under reduced pressure and the cake was dissolved in DCM, washed with brine, dried over Na₂SO₄ and evaporated to dryness to give the desired adduct.

Yield: 99% (445 mg).

¹H-NMR (300 MHz, DMSO-d₆) δ: 7.07 (d, 1H), 6.98 (dd, 1H), 6.89 (d, 1H), 4.97 (d, 1H), 4.41 (t, 1H), 4.18 (m, 1H), 3.36 (dd, 1H), 3.19 (dd, 1H) 2.98 (dd, 1H), 2.79 (m, 1H), 2.63 (dd, 1H), 2.11 (m, 1H), 1.85-1.15 (m, 6H), 1.16 (d, 6H), 1.07 (s, 3H), 0.94 (s, 3H).

MS: 302 (M⁺).

Step E: 6-oxo-13-isopropylpodocarpa-8,11,13-triene-15-aldehyde 312 mg of 13-isopropylpodocarpa-8,11,13-triene-6α,15-diol in 4 ml of dry DCM were added to a suspension of 667 mg of PCC in 4 ml of dry DCM and stirred at RT for 2 hours. The reaction mixture was then poured into 40 ml of Et₂O. The black mixture was littered on a florisil pad. The filtrate was evaporated and the resume was purified by flash chromatography using n-hexane/AcOEt 9/1 to give the desired adduct.

Yield: 45% (138 mg).

¹H-NMR (300 MHz, DMSO-d₆) δ: 9.25 (s, 1H), 7.28 (d, 1H), 7.14 (dd, 1H), 7.02 (d, 1H), 3.81 (d, 1H), 3.57 (d, 1H), 2.89 (s, 1H), 2.84 (m, 1H), 2.31 (m, 1H) 1.80-1.50 (m, 5H), 1.22 (s, 3H), 1.18 (d, 6H), 1.15 (s, 3H).

MS; 298 (M⁺).

Step F: (E)-15-(2-aminoethoxyimino)-13-isopropylpodocarpa-8,11,13-triene-6-one fumarate A solution of 154 mg of 2-aminoethoxyamine dihydrochloride and 165 mg of Na₂HPO₄.12H₂O in 1 ml of water was added to a solution of 138 mg of 6-oxo-13-isopropylpodocarpa-8,11,13-triene-15-aldehyde in 2 ml of THF and the reaction mixture was stirred overnight. NaCl was added, the phases were separated and the aqueous one extracted with THF. The combined organic extracts were evaporated. The residue was purified by flash chromatography DCM/MeOH/NH₄OH 90/10/1 as eluent. The solvent was removed under reduced pressure and the resulting residue was dissolved in MeOH before adding a stoichiometric amount of fumaric acid. The solution was then evaporated to dryness to give the desired adduct.

Yield: 70% (153 mg).

¹H-NMR (300 MHz, DMSO-d₆) δ: 8.02 (bb, 4H), 7.43 (s, 1H), 7.27 (d, 1H), 7.11 (dd, 1H), 6.97 (d, 1H), 6.39 (s, 2H), 3.96 (t, 2H), 3.68 (s, 2H), 2.88 (m, 2H), 2.82 (m, 1H), 2.81 (s, 1H), 2.33 (m, 1H), 1.80-1.30 (m, 5H), 1.37 (s, 3H), 1.17 (d, 6H), 1.11 (s, 3H),

MS: 356 (M⁺).

Example 12

(E)-15-(2-Aminoethoxyimino)-13-isopropylpodocarpa-8,11,13-triene-7-one fumarate

Step A: 13-isopropylpodocarpa-8,11,13-triene-7,15-diol

A 700 mg solution of methyl 7-oxo-13-isopropylpodocarpa-8,11,13-triene-15-carboxylate in 20 ml of dry THF was dropped into a stirred suspension of 810 mg of LiAlH₄ in 15 ml of dry THF at 0° C. The reaction mixture was heated to reflux for 1 hour and then cooled to 0° C. The reaction mixture was quenched by addition of 0.82 ml of H₂O, 0.82 ml of 30% NaOH and 2.4 ml of H₂O. After warming to RT, the reaction mixture was filtered and the resulting filtrate rinsed with AcOEt and DCM. The organic layer was concentrated under reduced pressure and the resulting residue was dissolved in DCM, washed with brine, dried over Na₂SO₄ and evaporated to dryness to give the desired adduct.

Yield: 55% (350 mg).

¹H-NMR (300 MHz, DMSO-d₆) δ: 7.30 (d, 1H), 7.10 (d, 1H), 6.99 (dd, 1H), 5.09 (d, 1H), 4.50 (m, 2H), 3.27 (dd, 1H), 2.90 (dd, 1H), 2.79 (m, 1H), 2.22 (m, 1H), 1.96 (dd, 1H), 1.80-1.40 (m, 7H), 1.17 (s, 3H), 1.16 (d, 6H), 0.75 (s, 3H).

MS: 302 (M⁺).

Step B: 7-oxo-13-isopropylpodocarpa-8,11,13-triene-15-aldehyde 1.30 g of IBX were added to a stirred solution of 350 mg of 13-isopropylpodocarpa-8,11,13-triene-7,15-diol in 7 ml of DMSO. After 1 hour the solution was quenched with 40 ml of water followed by 40 ml of Et₂O. The reaction mixture was filtered and the filtrate thoroughly rinsed with Et₂O. The phases were separated and the organic extract was concentrated under reduced pressure. The resulting residue was purified by flash chromatography using n-hexane/AcOEt 95/5 to give the desired adduct.

Yield: 75% (250 mg).

¹H-NMR (300 MHz, DMSO-d₆) δ: 9.25 (s, 1H), 7.70 (d, 1H), 7.51 (dd, 1H), 7.42 (d, 1H), 2.92 (m, 1H), 2.74 (dd, 1H), 2.44 (dd, 1H), 2.39 (m, 1H), 1.97 (dd, 1H), 1.87-1.25 (m, 5H), 1.22 (s, 3H), 1.18 (d, 6H), 1.12 (s, 3H).

MS: 298 (M⁺).

Step C: (E)-15-(2-aminoethoxyimino)-13-isopropylpodocarpa-8,11,13-triene-one fumarate The desired adduct has been synthesized following the experimental conditions described in example 1, using 7-oxo-13-isopropylpodocarpa-8,11,13-triene-15-aldehyde instead of 13-isopropylpodocarpa-8,11,13-triene-15-aldehyde. The title compound was also triturated in Et2O to afford a white solid.

Yield: 88% (188 mg).

¹H-NMR (300 MHz, DMSO-d₆) δ: 8.20 (bb, 4H), 7.69 (d, 1H), 7.50 (dd, 1H), 7.41 (d, 1H), 7.27 (s, 1H), 6.38 (s, 2H), 4.03 (m, 2H), 2.93 (m, 3H), 2.72 (dd, 1H), 2.38 (m, 1H), 2.28 (dd, 1H), 2.17 (dd, 1H), 1.90-1.35 (m, 5H), 1.23 (s, 3H), 1.18 (d, 6H), 1.16 (s, 3H).

MS: 356 (M⁺).

Example 13

(E)-15-(3-Aminopropoxyimino)-13-isopropylpodocarpa-8,11,13-triene-7-one fumarate It has been synthesized according to the method described in example 12 and using 3-aminopropoxyamine drihydrochloride instead of 2-aminoethoxyamine dihydrochloride in STEP C. The title compound was obtained as a white solid.

Yield: 79% (90 mg).

$^1$H-NMR (300 MHz, DMSO-d$_6$) δ: 8.20 (bb, 4H), 7.69 (d, 1H), 7.50 (dd, 1H), 7.41 (d, 1H), 7.24 (s, 1H), 6.36 (s, 2H), 3.99 (m, 2H), 2.91 (m, 1H), 2.78 (m, 2H), 2.72 (dd, 1H), 2.38 (m, 1H), 2.23 (dd, 1H), 2.15 (dd, 1H), 1.85-1.35 (m, 7H), 1.23 (s, 3H), 1.18 (d, 6H), 1.15 (s, 3H).

MS: 370 (M$^+$).

Example 14

(E)-15-(3-Aminopropoxyimino)-13-isopropylpodocarpa-8,11,13-triene-6-one fumarate It has been synthesized according to the method described in example 11 and using 3-aminopropoxyamine dihydrochloride instead of 2-aminoethoxyamine dihydrochloride in STEP F. The title compound was obtained as a white solid.

Yield: 61% (134 mg).

$^1$H-NMR (300 MHz, DMSO-d$_6$) δ: 7.70 (bb, 4H), 7.63 (s, 1H), 7.23 (d, 1H), 7.07 (dd, 1H), 6.93 (d, 1H), 6.60 (s, 2H), 3.90 (m, 2H), 3.59 (s, 2H), 2.79 (m, 4H), 2.29 (m, 1H), 1.80-1.30 (m, 7H), 1.34 (s, 3H), 1.14 (d, 6H), 1.08 (s, 3H).

MS: 370 (M$^+$).

Example 15

(E,E)-15-(2-Aminoethoxyimino)-6-hyroxyimino-13-isopropylpodocarpa-8,11,13-triene fumarate A mixture of 139 mg of (E)-15-(2-aminoethoxyimino)-13-isopropylpodocarpa-8,11,13-triene-6-one fumarate and 309 mg of hydroxylamine hydrochloride in 3.5 ml of pyridine was stirred at RT for 3 days and at 70° C. for 6 hours afterwards. The mixture was then cooled and pyridine was removed under reduced pressure. The crude reaction mixture was purified by flash chromatography using DCM/MeOH/NH$_4$OH 93/7/0.7 as eluent. After removal of the solvent under vacuum, a stoichiometric amount of fumaric acid was added and the solution was evaporated to dryness to afford the title compound as a white solid.

Yield: 20% (28 mg).

$^1$H-NMR (300 MHz, DMSO-d$_6$) δ: 10.85 (s, 1H), 8.50 (bb, 4H), 7.54 (s, 1H), 7.21 (d, 1H), 7.04 (dd, 1H), 7.01 (d, 1H), 6.42 (s, 2H), 3.98 (t, 2H), 3.81 (d, 1H), 3.57 (d, 1H), 2.94 (t, 2H), 2.80 (m, 1H), 2.49 (s, 1H), 2.34 (m, 1H), 1.85-1.35 (m, 5H), 1.47 (s, 3H), 1.16 (d, 6H), 1.06 (s, 3H).

MS: 371 (M$^-$).

Example 16

(E,E)-15-(2-Aminoethoxyimino)-7-hydroxyimino-13-isopropylpodocarpa-8,11,13-triene fumarate It has been synthesized according to the method described in example 15 and using (E)-15-(2-aminoethoxyimino)-13-isopropylpodocarpa-8,11,13-triene-7-one fumarate instead of (E)-15-(2-aminoethoxyimino)-13-isopropylpodocarpa-8,11,13-triene-6-one fumarate. The title compound was obtained as a white solid.

Yield: 62% (45 mg).

$^1$-NMR (300 MHz, DMSO-d$_6$) δ: 12.90 (bb, 1H), 11.17 (s, 1H), 7.98 (bb, 3H), 7.66 (d, 1H), 7.30 (s, 1H), 7.21 (m, 2H), 6.60 (s, 2H), 4.10 (t, 2H), 8.03 (t, 2H), 2.85 (m, 1H), 2.63 (dd, 1H), 2.37 (dd, 1H), 2.30 (m, 1H), 1.85-1.35 (m, 3H), 1.19 (s, 3H), 1.16 (d, 6H), 1.04 (s, 3H).

MS: 371 (M$^+$).

Example 17

(E,E)-15-(3-Aminpropoxyimino)-7-hydroxyimino-13-isopropylpodocarpa-8,11,13-triene fumarate It has been synthesized according to the method described in example 16 and using (E)-15-(3-aminopropoxyimino)-13-isopropylpodocarpa-8,11,13-triene-7-one fumarate instead of (E)-15-(2-aminoethoxyimino)-13-isopropylpodocarpa-8,11,13-triene-7-one fumarate. The title compound was obtained as a white solid.

Yield: 58% (45 mg).

$^1$-NMR (300 MHz, DMSO-d$_6$) δ: 12.90 (bs, 1H), 11.16 (s, 1H) 7.88 (bb, 3H), 7.25 (s, 1H), 7.23 (d, 1H), 7.18 (dd, 1H), 6.60 (s, 2H), 3.99 (t, 2H), 2.82 (m, 3H), 2.60 (dd, 1H), 2.35 (dd, 1H), 2.29 (m, 1H), 1.93-1.35 (m, 8H), 1.17 (s, 3H), 1.16 (d, 6H), 1.04 (s, 3H).

MS: 385 (M$^+$).

Example 18

(E,E)-6,15-dihydroxyimino-13-isopropylpodocarpa-8,11,13-triene

It has been synthesized according to the method described in example 15 and using 6-oxo-13-isopropylpodocarpa-8,11,13-triene-15-aldehyde instead of (E)-15-(2-aminoethoxyimino)-13-isopropylpodocarpa-8,11,13-triene-6-one fumarate. The title compound was obtained as a white solid.

Yield: 29% (28 mg).

$^1$H-NMR (300 MHz, DMSO-d$_6$) δ: 10.73 (s, 1H), 10.05 (s, 1H), 7.36 (s, 1H), 7.20 (d, 1H), 7.04 (dd, 1H), 7.00 (d, 1H), 3.82 (d, 1H), 3.52 (d, 1H), 2.80 (m, 1H), 2.46 (s, 1H), 2.34 (m, 1H), 1.85-1.35 (m, 5H), 1.47 (s, 3H), 1.16 (d, 6H), 1.06 (s, 3H).

MS: 328 (M$^+$).

Example 19

(E)-15-(2-Aminoethoxyimino)-6α-hydroxy-13-isopropylpodocarpa-8,11,13-triene-7-one fumarate Step A: 13-isopropylpodocarpa-8,11,13-triene-8,11,13-triene-6α,7,15-triol The title compound was obtained following the procedure described in Example 12-STEP A and using methyl 6α-acetoxy-7-oxo-13-isopropylpodocarpa-8,11,13-triene-15-carboxylate instead of methyl 7-oxo-13-isopropylpodocarpa-8,11,13-triene-15-carboxylate.

Yield: 97% (820 mg).

13-Isopropylpodocarpa-8,11,13-triene-6α,7α,15-triol $^1$H-NMR (300 MHz, DMSO-d$_6$) δ: 7.27 (d, 1H), 7.09 (d, 1H), 7.04 (dd, 1H), 5.09 (d, 1H), 4.69 (t, 1H), 4.66 (d, 1H), 4.10 (m, 2H), 3.90 (dd, 1H), 3.04 (dd, 1H), 2.84 (m, 1H), 2.13 (m, 1H), 1.85-1.22 (m, 6H), 1.18 (d, 6H), 1.12 (s, 3H), 0.96 (s, 3H).

13-Isopropylpodocarpa-8,11,13-triene-6α,7β,15-triol $^1$H-NMR (300 MHz, DMSO-d$_6$) δ: 7.24 (d, 1H), 7.10 (d, 1H), 7.02 (dd, 1H), 5.26 (d, 1H), 4.97 (d, 1H), 4.36 (m, 2H), 3.88 (m, 1H), 3.52 (d, 1H), 3.14 (dd, 1H), 2.81 (m, 1H), 2.19 (m, 1H), 1.80-1.15 (m, 6H), 1.20 (s, 3H), 1.17 (d, 6H), 0.97 (s, 3H).

MS: 318 (M$^+$).

Step B: 6α-hydroxy-7-oxo-13-isopropylpodocarpa-8,11,13-triene-15-aldehyde

The title compound, which was purified by flash chromatography using n-hexane/AcOEt 75/25, was obtained following the procedure described in Example 12-STEP B and using 13-isopropylpodocarpa-8,11,13-triene-6α,7,15-triol instead of 13-isopropylpodocarpa-8,11,13-triene-7,15-diol.

Yield: 65% (520 mg).

$^1$H-NMR (300 MHz, DMSO-$d_6$) δ: 9.09 (s, 1H), 7.76 (d, 1H), 7.53 (dd, 1H), 7.44 (d, 1H), 5.70 (d, 1H), 4.37 (dd, 1H), 2.94 (m, 1H), 2.38 (m, 2H), 1.85-0.95 (m, 5H), 1.30 (s, 3H), 1.22 (s, 3H), 1.19 (d, 6H).

MS: 314 ($M^+$).

Step C: (E)-15-(2-aminoethoxyimino)-6α-hydroxy-13-isopropylpodocarpa-8,11,13-triene-7-one fumarate The title compound was obtained as a white solid following the procedure described in Example 1 but carrying out the reaction for two days (instead of 1 hour), and using 6α-hydroxy-7-oxo-13-isopropylpodocarpa-8,11,13-triene-15-aldehyde instead of 13-isopropylpodocarpa-8,11,13-triene-15-aldehyde.

Yield: 30% (150 mg).

$^1$H-NMR (300 MHz, DMSO-$d_6$) δ: 12.60 (bb, 1H), 8.60 (bb, 3H), 7.70 (d, 1H), 7.48 (dd, 1H), 7.39 (d, 1H), 7.38 (s, 1H), 6.87 (s, 2H), 5.20 (bb, 1H), 4.45 (d, 1H), 3.95 (m, 2H), 2.91 (m, 3H), 2.32 (m, 1H), 2.07 (d, 1H), 1.85-1.20 (m, 5H), 1.31 (s, 3H), 1.27 (s, 3H), 1.15 (d, 1H).

MS: 372 ($M^+$).

Example 20

(E)-15-(3-Aminopropoxyimino)-6α-hydroxy-13-isopropylpodocarpa-8,11,13-triene-7-one fumarate The title compound was obtained as a white solid following the procedure described in Example 19-STEP C and using 3-aminopropoxyamine dihydrochloride instead of 2-aminoethoxyamine dihydrochloride in STEP C.

Yield: 38% (143 mg).

$^1$H-NMR (300 MHz, DMSO-$d_6$) δ: 8.30 (bb, 4H), 7.73 (d, 1H), 7.52 (dd, 1H), 7.42 (d, 1H), 7.34 (s, 1H), 6.37 (s, 2H), 5.31 (bb, 1H), 4.45 (d, 1H), 3.91 (m, 2H), 2.93 (m, 1H), 2.80 (m, 2H), 2.35 (m, 1H), 2.08 (d, 1H), 1.9-1.30 (m, 7H), 1.34 (s, 3H), 1.29 (s, 3H), 1.19 (d, 6H).

MS: 386 ($M^+$).

Example 21

(E,E)-15-(3-Aminopropoxyimino)-7-hydroxyimino-13-isopropylpodocarpa-8,11,13-triene-6α-ol fumarate The title compound was obtained as a white solid following the procedure described in Example 16 and using (E)-15-(3-aminopropoxyimino)-6α-hydroxy-13-isopropylpodocarpa-8,11,13-triene-7-one fumarate instead of (E)-15-(2-aminoethoxyimino)-13-isopropylpodocarpa-8,11,13-triene-7-one.

Yield: 38% (54 mg).

$^1$H-NMR (300 MHz, DMSO-$d_6$) δ: 11.70 (bb, 1H), 8.70 (m, 4H), 7.42 (d, 1H), 7.31 (s, 1H), 7.22 (dd, 1H), 7.16 (d, 1H), 6.37 (s, 2H), 4.89 (d, 1H), 4.70 (bb, 1H), 3.91 (m, 2H), 2.87 (m, 1H), 2.78 (m, 2H), 2.15 (m, 1H), 1.90-1.30 (m, 8H), 1.30 (s, 3H), 1.18 (d, 6H), 0.96 (s, 3H).

MS: 401 ($M^-$).

Example 22

(E,E)-15-(2-Aminoethoxyimino)-7-hydroxyimino-13-isopropylpodocarpa-8,11,13-triene-6α-ol fumarate The title compound was obtained as a white solid following the procedure described in Example 21 and using (E)-15-(2-aminoethoxyimino)-6α-hydroxy-13-isopropylpodocarpa-8,11,13-triene-7-one fumarate instead of (E)-15-(3-aminopropoxyimino)-6α-hydroxy-13-isopropylpodocarpa-8,11,13-triene-7-one fumarate.

Yield: 30% (80 mg).

$^1$H-NMR (300 MHz, DMSO-$d_6$) δ: 11.60 (bb, 1H), 8.50 (bb, 4H), 7.42 (d, 1H), 7.37 (s, 1H), 7.22 (dd, 1H), 7.17 (d, 1H), 6.38 (s, 2H), 4.89 (d, 1H), 5.05 (bb, 1H), 3.98 (m, 2H), 2.84 (m, 2H), 2.86 (m, 1H), 2.15 (m, 1H), 1.79-1.25 (m, 6H), 1.31 (s, 3H), 1.18 (d, 6H), 0.96 (s, 3H).

MS: 387 ($M^+$).

Example 23

(Z)-15-(4-Aminobutyliden)-13-isopropylpodocarpa-8,11,13-triene fumarate

Step A: (Z)-15-(3-cyanopropyliden)-13-isopropylpodocarpa-8,11,13-triene KOtBu (310 mg) was added portionwise to a stirred suspension of 1.16 g of (3-cyanopropyl)triphenylphosphonium bromide in 8 ml of dry THF at 0° C. After 30 minutes at 0° C., the mixture was warmed to RT and a solution of 0.20 g of 13-isopropylpodocarpa-8,11,13-triene-15-aldehyde in 6 ml of dry THF was added. The reaction mixture was stirred for 45 minutes and was then quenched by addition of 60 ml of 5% aqueous $NaH_2PO_4$ and AcOEt. The phases were separated and the aqueous layer was extracted with AcOEt. The combined organic extracts were dried over $Na_2SO_4$ and the solvent was removed under reduced pressure. The residue was purified by flash chromatography using n-hexane/AcOEt 9/1 to give the desired adduct.

Yield: 98% (230 mg).

$^1$H-NMR (300 MHz, Acetone-$d_6$) δ: 7.17 (d, 1H), 6.98 (d, 1H), 6.87 (d, 1H), 5.37 (m, 1H), 5.24 (m, 1H), 2.90-2.50 (m, 7H), 2.32 (m, 1H), 1.85-1.31 (m, 8H), 1.27 (s, 3H), 1.20 (s, 3H), 1.19 (d, 6H).

MS: 335 ($M^+$).

Step B: (Z)-15-(4-aminobutyliden)-13-isopropylpodocarpa-8,11,13-triene fumarate

Na (2.3 g in pieces) was added over a four hour period to a solution of 250 mg of (Z)-15-(3-cyanopropyliden)-13-isopropylpodocarpa-8,11,13-triene in 25 ml of EtOH at reflux under stirring. The mixture was cooled to RT, and 50 ml of a 5% aqueous solution of $NaH_2PO_4$ were added followed by 1N HCl until pH 8 was reached. The reaction mixture was extracted with DCM (3×100 ml) and the organic phases were concentrated under reduced pressure. The residue was purified by flash chromatography using DCM/MeOH/$NH_4OH$ 90/10/1 as eluent. After removal of the solvent under vacuum, the residue was dissolved in MeOH and a stoichiometric amount of fumaric acid was added. MeOH was removed under reduced pressure to Afford the desired adduct as a white solid.

Yield: 95% (243 mg).

$^1$-NMR (300 MHz, DMSO-$d_6$) δ: 7.87 (bb, 4H), 7.14 (d, 1H), 6.95 (dd, 1H), 6.82 (d, 1H), 6.41 (s, 2H), 5.16 (m, 2H), 2.76 (m, 5H), 2.22 (m, 3H), 1.80-1.20 (m, 10H), 1.17 (s, 3H), 1.14 (d, 6H), 1.13 (s, 3H).

MS: 339 (M$^+$).

Example 24

(Z)-15-(5-Aminopentyliden)-13-isopropylpodocarpa-8,11,13-triene fumarate

Step A: (Z)-15-(4-cyanobutyliden)-13-isopropylpodocarpa-8,11,13-triene

The title compound was obtained following the procedure described in Example 23-STEP A and using (4-cyanobutyl) triphenylphospbonium bromide instead of (3-cyanopropyl) triphenylphosphonium bromide.

Yield: 92% (450 mg).

$^1$H-NMR (300 MHz, Acetone-$d_6$) δ: 7.17 (d, 1H), 6.97 (dd, 1H), 6.87 (d, 1H), 5.29 (m, 1H), 5.20 (m, 1H), 2.95-2.25 (m, 8H), 1.90-1.25 (m, 10H), 1.26 (s, 3H), 1.20 (s, 3H), 1.19 (d, 6H).

MS: 349 (M$^+$).

Step B: (Z)-15-(5-aminopentyliden)-13-isopropylpodocarpa-8,11,13-triene fumarate The title compound was obtained as a white solid following the procedure described in Example 23-STEP B and using (Z)-15-(4-cyanobutyliden)-13-isopropylpodocarpa-8,11,13-triene instead of (Z)-15-(3-cyanopropyliden)-13-isopropylpodocarpa-8,11,13-triene.

Yield: 80% (260 mg).

$^1$H-NMR (300 MHz, DMSO-$d_6$) δ: 7.98 (bb, 4H), 7.13 (d, 1H), 6.94 (dd, 1H), 6.82 (d, 1H), 6.40 (s, 2H), 5.14 (m, 2H), 2.74 (m, 5H), 2.26 (m, 1H), 2.17 (m, 2H), 1.77-1.20 (m, 12H), 1.16 (s, 3H), 1.14 (d, 6H), 1.12 (s, 3H).

MS: 353 (M$^+$).

Example 25

15-(4-Aminobutyl)-13-isopropylpodocarpa-8,11,13-triene fumarate

A mixture of 400 mg of (Z)-15-(4-aminobutyliden)-13-isopropylpodocarpa-8,11,13-triene and 130 mg of 10% Pd/C in 50 ml of absolute EtOH was hydrogenated at RT under a one atmosphere pressure of $H_2$ for 2 hours. The catalyst was filtered off, and the solvent was removed under vacuum. The crude reaction mixture was purified by flash chromatography using DCM/MeOH/NH$_4$OH 90/10/1 as eluent. After removal of the solvent under reduced pressure, the residue was dissolved in MeOH and a stoichiometric amount of fumaric acid was added. MeOH was removed under reduced pressure to afford the desired adduct as a white solid.

Yield: 65% (350 mg).

$^1$H-NMR (300 MHz, DMSO-$d_6$) δ: 8.00 (bb, 4H), 7.13 (d, 1H), 6.93 (dd, 1H), 6.82 (d, 1H), 6.40 (s, 2H), 2.77 (m, 5H), 2.25 (m, 1H), 1.80-1.10 (m, 16H), 1.13 (d, 6H), 1.12 (s, 3H), 0.86 (s, 3H).

MS: 341 (M$^+$).

Example 26

15-(4-Aminopentyl)-13-isopropylpodocarpa-8,11,13-triene fumarate

The title compound was obtained as a white solid following the procedure described in Example 25 and using (Z)-15-(5-aminopentyliden)-13-isopropylpodocarpa-8,11,13-triene fumarate instead of (Z)-15-(4-aminobutyliden)-13-isopropylpodocarpa-8,11,13-triene.

Yield: 69% (385 mg).

$^1$H-NMR (300 MHz, DMSO-$d_6$) δ: 8.00 (bb, 4H), 7.13 (d, 1H), 6.93 (dd, 1H), 6.81 (d, 1H), 6.61 (s, 2H), 2.75 (m, 5H), 2.24 (m, 1H), 1.80-1.10 (m, 18H), 1.13 (d, 6H), 1.11 (s, 3H), 0.86 (s, 3H).

MS: 355 (M$^+$).

Example 27

15-(3-Aminopropoxy)-13-isopropylpodocarpa-8,11,13-triene fumarate

Step A: 13-isopropyl-15-allyloxypodocarpa-8,11,13-triene

A solution of 571 mg of 13-isopropylpodocarpa-8,11,13-triene-15-ol (González M. A., et al., *Eur. J. Med. Chem.*, 2010, 45, 811) in 5 ml of 1,2-dimethoxyethane was added into a stirred suspension of 490 mg of NaH (60% in oil) and 49 mg of NaI in 5 ml of 1,2-dimethoxyethane. After 15 minutes, 1.75 ml of allyl bromide were added and the reaction mixture was stirred for 2 hours. 10 ml of MeOH/H$_2$O 1/1 were added and the phases were separated. The aqueous phase was extracted with Et$_2$O and the combined organic extracts were dried over Na$_2$SO$_4$ and the solvent was removed under vacuum. The residue was purified by flash chromatography using n-hexane/AcOEt 98/2 to afford the desired adduct.

Yield: 79% (511 mg).

$^1$H-NMR (300 MHz, Acetone-$d_6$) δ: 7.17 (d, 1H), 6.96 (dd, 1H), 6.87 (d, 1H), 5.89 (m, 1H), 5.24 (m, 1H), 5.09 (m, 1H), 3.95 (m, 2H), 3.32 (d, 1H), 2.98 (d, 1H), 2.83 (m, 3H), 2.31 (m, 1H), 1.90-1.25 (m, 8H), 1.19 (s, 3H), 1.18 (d, 6H), 0.89 (s, 3H).

MS: 312 (M$^+$).

Step B: 13-isopropyl-15-(3-hydroxypropoxy)podocarpa-8,11,13-triene

To a solution of 510 mg of 13-isopropyl-15-allyloxypodocarpa-8,11,13-triene in 10 ml of dry THF at 0° C., 960 mg of 9-BBN were added. After 1 hour the mixture was warmed to RT and was stirred for 2 days. The reaction was completed alter a further hour at reflux. After cooling to RT, 17 ml of EtOH were added followed by 0.31 ml of 6N NaOH and 0.36 ml of 30% H$_2$O$_2$. After 3 hours the solvent was evaporated and the residue was taken up with Et$_2$O and water. The phases were separated and the organic layer was dried over Na$_2$SO$_4$ and evaporated under vacuum. The residue was purified by flash chromatography using n-hexane/AcOEt 8/2. Alter removal of the solvent under reduced pressure, the desired adduct was obtained as a 3/7 mixture of 13-isopropyl-15-(3-hydroxypropoxy)podocarpa-8,11,13-triene and 13-isopropyl-15-(2-hydroxy-propoxy)podocarpa-8,11,13-triene.

Yield: (515 mg).

$^1$-NMR (300 MHz, Acetone-$d_6$) δ: 7.17 (d, 1H), 6.96 (dd, 1H), 6.86 (d, 1H), 4.45-1.20 (m, 21H), 1.19 (s, 3H), 1.18 (d, 6H), 0.88 (s, 3H).

MS: 330 (M$^+$).

Step C: 13-isopropyl-15-(3-phthalimidopropoxy)podocarpa-8,11,13-triene

To a solution of 613 mg of a the above obtained 3/7 mixture in 20 ml of dry THF, 522 mg of phthalimide and 931 mg of triphenylphosphine were added. The reaction mixture was cooled to 0° C. and 0.70 mL of DIAD was added. After 24 hours, the solvent was evaporated and the residue was taken up with Et$_2$O. The reaction mixture was filtered and the filtrate evaporated under vacuum. The residue was purified by flash chromatography using n-hexane/AcOEt 9/1 to afford the desired adduct.

Yield: 24% (200 mg, 2 steps).
$^1$H-NMR (300 MHz, Acetone-d$_6$) δ: 7.77 (m, 4H), 7.13 (d, 1H), 6.96 (dd, 1H), 6.86 (d, 1H), 3.73 (m, 2H), 3.47 (m, 2H), 3.27 (d, 1H), 2.91 (d, 1H), 2.82 (m, 3H), 2.35-1.40 (m, 11H), 1.20 (s, 3H), 1.17 (d, 6H), 0.83 (s, 3H).
MS: 459 (M$^+$).

Step D: 15-(3-aminopropoxy)-13-isopropylpodocarpa-8,11,13-triene fumarate

A solution of 199 mg of 15-(3-phtalimidopropoxy)-13-isopropylpodocarpa-8,11,13-triene and 0.62 ml of hydrazine hydrate in 5 ml of absolute EtOH was heated to reflux for 3 hours. After cooling, the mixture was filtered and the solvent was removed under vacuum. The residue was purified by flash chromatography using DOM/MeOH/NH$_4$OH 93/7/0.7 as eluent. After removal of the solvent under reduced pressure, the residue was dissolved in MeOH and a stoichiometric amount of fumaric acid was added. MeOH was removed under reduced pressure to afford the desired adduct as a white solid.

Yield: 57% (110 mg).
$^1$H-NMR (300 MHz, DMSO-d$_6$) δ: 8.19 (bb, 4H), 7.14 (d, 1H), 6.93 (dd, 1H), 6.82 (d, 1H), 6.40 (s, 2H), 3.39 (m, 2H), 3.22 (d, 1H), 2.89 (d, 1H), 2.76 (m, 5H), 2.24 (m, 1H), 1.80-1.10 (m, 10H), 1.14 (m, 6H), 1.11 (s, 3H), 0.81 (s, 3H).
MS: 343 (M$^+$).

Example 28

15-(3-Aminopropylthio)-13-isopropylpodocarpa-8,11,13-triene fumarate

Step A: 13-isopropyl-15-methanesulphonyloxypodocarpa-8,11,13-triene 0.57 ml of NEt$_3$ was added to a solution of 1.02 g of 13-isopropylpodocarpa-8,11,13-triene-15-ol (González M. A., et al., *Eur. J. Med. Chem.*, 2010, 45, 811) in 15 ml of DCM. After cooling to 0° C., 0.29 ml of methanesulphonyl chloride was added. The reaction mixture was stirred for 1.5 hours at RT. H$_2$O was added and the phases were separated. The aqueous phase was extracted with DCM. The combined organic extracts were washed with 0.5N HCl, water and brine. After removal of the solvent under vacuum, the desired adduct as a white solid.

Yield: 94% (1.21 g).
$^1$-NMR (300 MHz, Acetone-d$_6$) δ: 7.18 (d, 1H), 6.98 (dd, 1H), 6.88 (d, 1H), 4.13 (d, 1H), 3.85 (d, 1H), 3.11 (s, 3H), 2.85 (m, 3H), 2.34 (m, 1H), 1.90-1.25 (m, 8H), 1.22 (s, 3H), 1.18 (d, 6H), 0.99 (s, 3H).
MS: 350 (M$^+$).

Step B: 13-isopropyl-15-(3-hydroxypropylthio)podocarpa-8,11,13-triene

A solution of 0.90 ml of 3-mercaptopropanol in 12 ml of HMPA and 3.0 ml of DMF was degassed with Ar and cooled to 0° C. 0.40 g of NaH (60% in oil) was added and the reaction mixture was stirred for 10 minutes. A solution of 1.20 g of 13-isopropyl-15-methanesulphonyloxypodocarpa-8,11,13-triene in 3 ml of HMPA and 2.0 ml of DMF was added. The reaction mixture was heated to 130° C. and was stirred at this temperature for 30 minutes. The reaction mixture was then cooled and 250 of water were added before being extracted three times with Et$_2$O. The combined organic extracts were washed with water, dried over Na$_2$SO$_4$ and the solvent was removed under reduced pressure. The residue was purified by flash chromatography using n-hexane/AcOEt 75/25 to afford the desired adduct.

Yield: 89% (1.20 g).
$^1$H-NMR (300 MHz, Acetone-d$_6$) δ: 7.17 (d, 1H), 6.97 (dd, 1H), 6.88 (d, 1H), 3.62 (m, 2H), 3.53 (m, 1H), 2.83 (m, 3H), 2.77 (d, 1H), 2.58 (t, 2H), 2.44 (d, 1H), 2.81 (m, 1H), 1.90-1.25 (m, 10H), 1.19 (s, 3H), 1.18 (d, 6H), 1.03 (s, 3H).
MS: 346 (M$^+$).

Step C: 13-isopropyl-15-(3-phthalimidopropylthio)podoearpa-8,11,13-triene

The title compound was obtained as a white solid following the procedure described in Example 27-STEP C and using 13-isopropyl-15-(3-hydroxypropylthio)podocarpa-8,11,13-triene instead of 13-isopropyl-15-(3-hydroxypropoxy)podocarpa-8,11,13-triene.

Yield: 92% (1.30 g).
$^1$H-NMR (300 MHz, Acetone-d$_6$) δ: 7.83 (m, 4H), 7.16 (d, 1H), 6.96 (dd, 1H), 6.84 (d, 1H), 3.76 (t, 2H), 2.80 (m, 4H), 2.58 (t, 2H), 2.42 (d, 1H), 2.29 (m, 1H), 1.96 (m, 2H), 1.85-1.19 (m, 8H), 1.19 (d, 6H), 1.17 (s, 3H), 1.01 (s, 3H).
MS: 475 (M$^+$).

Step D: 15-(3-aminopropylthio)-13-isopropylpodocarpa-8,11,13-triene fumarate

The title compound was obtained as a white solid following the procedure described in Example 27-STEP D and using 15-(3-phtalimidopropylthio)-13-isopropylpodocarpa-8,11,13-triene instead of 15-(3-phtalimidopropoxy)-13-isopropylpodocarpa-8,11,13-triene.

Yield: 61% (138 mg).
$^1$H-NMR (300 MHz, DMSO-d$_6$) δ: 8.00 (bb, 4H), 7.13 (d, 1H), 6.94 (dd, 1H), 6.83 (d, 1H), 6.40 (s, 2H), 2.80 (m, 5H), 2.67 (d, 1H), 2.51 (t, 2H), 2.39 (d, 1H), 2.25 (m, 1H), 1.80-1.20 (m, 10H), 1.14 (d, 6H), 1.11 (s, 3H), 0.95 (s, 3H).
MS: 359 (M$^+$).

Example 29

(E)-15-(2-Aminoethoxyimino)-13-isopropylpodocarpa-8,11,13-triene-6α-ol fumarate

Step A: 6α-hydroxy-13-isopropylpodocarpa-8,11,13-triene-15-aldehyde

The title compound was obtained following the procedure described in Example 12-STEP B and using 13-isopropylpodocarpa-8,11,13-triene-6α,15-diol instead of 13-isopropylpodocarpa-8,11,13-triene-7,15-diol.

Yield: 46% (125 mg).
$^1$-NMR (300 MHz, DMSO-d$_6$) δ: 9.14 (s, 1H), 7.16 (d, 1H), 6.98 (dd, 1H), 6.87 (d, 1H), 5.11 (d, 1H), 3.95 (m, 1H), 3.17 (dd, 1H), 2.78 (m, 1H), 2.68 (dd, 1H), 2.26 (m, 1H), 1.85 (d, 1H), 1.80-0.90 (m, 5H), 1.16 (s, 3H), 1.15 (d, 6H), 1.12 (s, 3H).
MS: 300 (M$^+$).

Step B: (E)-15-(2-aminoethoxyimino)-13-isopropylpodocarpa-8,11,13-triene-6α-ol fumarate A solution of 54 mg of 6α-hydroxy-13-isopropylpodocarpa-8,11,13-triene-15-aldehyde and 215 mg of 2-aminoethoxyamine dihydrochloride in 1 ml of pyridine was heated to 60° C. under stirring overnight. Pyridine was removed under vacuum and the crude reaction mixture was purified by flash chromatography using DCM/MeOH/NH₄OH 90/10/1 as eluent. The solvent was removed under vacuum and the residue was dissolved in MeOH and a stoichiometric amount of fumaric acid was added and the solution was evaporated to dryness under vacuum. The title compound was obtained as a white solid.

Yield: 50% (43 mg).

$^1$H-NMR (300 MHz, DMSO-$d_6$) δ: 8.09 (bb, 4H), 7.44 (s, 1H), 7.12 (d, 1H), 6.97 (dd, 1H), 6.86 (d, 1H), 6.38 (s, 2H), 4.79 (bb, 1H), 4.07 (m, 1H), 3.96 (t, 2H), 3.19 (dd, 1H), 2.92 (t, 2H), 2.77 (m, 1H), 2.65 (dd, 1H), 2.23 (m, 1H), 1.85-1.20 (m, 6H), 1.28 (s, 3H), 1.15 (d, 6H), 1.12 (s, 3H).

MS: 358 (M$^+$).

Example 30

(E)-15-(3-Aminopropoxyimino)-13-isopropylpodocarpa-8,11,13-triene-6α-ol fumarate The title compound was obtained as a white solid following the procedure described in Example 29-STEP B and using 3-aminopropoxyamine dihydrochloride instead of 2-aminoethoxyamine dihydrochloride.

Yield: 67% (57 mg).

$^1$H-NMR (300 MHz, DMSO-$d_6$) δ: 8.60 (m, 4H), 7.86 (s, 1H), 7.11 (d, 1H), 6.96 (dd, 1H), 6.86 (d, 1H), 6.40 (s, 2H), 1.95 (bb, 1H), 4.08 (m, 1H), 3.91 (m, 2H), 3.18 (dd, 1H), 2.82 (t, 2H) 2.77 (m, 1H), 2.65 (dd, 1H), 2.22 (m, 1H), 1.93-1.20 (m, 8H), 1.27 (s, 3H), 1.14 (d, 6H), 1.11 (s, 3H).

MS: 372 (M$^+$).

Example 31

(E)-15-(2-Aminoethoxyimino)-13-isopropylpodocarpa-7,13-diene fumarate

The title compound was obtained as a white solid following the procedure described in Example 1 and using 13-isopropylpodocarpa-7,13-diene-15-aldehyde (González M. A., et al., *Eur. J. Med. Chem.*, 2010, 45, 811) instead of 13-isopropylpodocarpa-8,11,13-triene-15-aldehyde.

Yield: 40% (40 mg).

$^1$H-NMR (300 MHz, DMSO-$d_6$) δ: 8.30 (bb, 4H), 7.22 (s, 1H), 6.41 (s, 2H), 5.71 (s, 1H), 5.33 (m, 1H), 4.04 (t, 2H), 2.95 (t, 2H), 2.30-1.00 (m, 15H), 1.08 (s, 3H), 0.95 (d, 6H), 0.76 (s, 3H).

MS: 314 (M$^-$).

Example 32

(E)-15-(3-Aminopropoxyimino)-13-isopropylpodocarpa-7,13-diene fumarate

The title compound was obtained as a white solid following the procedure described in Example 31 and using 3-aminopropoxyamine dihydrochloride instead of 2-aminoetoxyamine dihydrochloride.

Yield: 64% (38 mg).

$^1$H-NMR (300 MHz, DMSO-$d_6$) δ: 8.10 (bb, 4H), 7.17 (s, 1H), 6.35 (s, 2H), 5.71 (s, 1H), 5.34 (m, 1H), 3.96 (t, 2H), 2.75 (t, 2H), 2.30-1.00 (m, 17H), 1.07 (s, 3H), 0.96 (d, 6H), 0.76 (s, 3H).

MS: 358 (M$^+$).

Example 33

15-(4-Piperidinyloxyamino)-13-isopropylpodocarpa-8,11,13-triene fumarate

1N HCl was added to a solution of 230 mg of (E)-15-(4-piperidinyloxyimino)-13-isopropylpodocarpa-8,11,13-triene free base in 8 ml of MeOH until pH 3 was reached. Then, 58 mg of NaBH₃CN were added and the pH was continuously kept at 3 by addition of 0.3N HCl, the pH being controlled by means of a pHstat. The reaction mixture was stirred overnight. MeOH was then removed under reduced pressure and the aqueous residue was brought to pH 10-12 by addition of 4N NaOH. The reaction mixture was extracted three times with Et₂O; the organic phase was dried over Na₂SO₄ and evaporated to dryness. The residue was purified by flash chromatography using DCM/MeOH/NH₄OH 90/10/1 as eluent. The solvent was removed under vacuum and the residue was dissolved in MeOH and a stoichiometric amount of fumaric acid was added and the solution was evaporated to dryness under vacuum. The title compound was obtained as a white solid.

Yield: 65% (196 mg).

$^1$H-NMR (300 MHz, DMSO-$d_6$ and TFA) δ: 8.44 (bb, 1H), 8.34 (bb, 1H), 7.13 (d, 1H), 6.94 (dd, 1H), 6.80 (d, 1H), 6.60 (s, 2H), 4.01 (m, 1H), 3.22-2.68 (m, 9H), 2.25 (m, 1H), 2.05-1.15 (m, 13H), 1.13 (d, 6H), 1.11 (s, 3H), 0.93 (s, 3H).

MS: 384 (M$^+$).

BIOLOGICAL RESULTS

Anti-hypertensive property of various derivatives were looked at in vivo in three animal models of hypertension (i.e., mutant α-adducin congenic rats, ouabain-hypertensive rats and Milan hypertensive rats).

Mutant α-Adducin Congenic Rats (NA)

The compound of example 4 was administered by oral gavage at various doses for six weeks to rats bearing an α-adducin mutation (NA strain). Such mutation leading to hypertension and organ complication (Bianchi G., et al., *Proc. Natl. Acad. Sci.*, 1994, 91, 3999) was obtained by introgressing a segment of chromosome 14 containing the locus of α-adducin from Milan Hypertensive rats (MHS), having the mutant variant, into Milan Normotensive rats (MNS), carrying the wild type α-adducin variant (Tripodi G., et al., *Biochem. Biophys. Res. Commun.*, 2004, 324, 562). The systolic blood pressure (SBP) and heart rate (HR) after a six week treatment are reported in table 1 underneath.

TABLE 1

| Example 4 (µg/kg/day) | SBP, mmHg | HR, beats/min |
|---|---|---|
| (vehicle methocel 0.5%) | 164.4 | 412 |
| 1 | 150.6* | 415 |
| 10 | 150.6* | 425 |
| 100 | 147.5** | 421 |

Ouabain-Hypertensive Rats (OHR)

Hypertension was provoked by subcutaneous ouabain infusion (15 μg/kg/day) in normotensive rats as already described (Ferrari P., et al., *J. Pharmacol. Exp. Ther.*, 1998, 285, 83). The compounds were administered by oral gavage once a day for six weeks at the dose indicated in table 2 underneath.

TABLE 2

| Experiments | Compounds (μg/kg/day) | | SBP, mmHg | HR, beats/min |
|---|---|---|---|---|
| A | (vehicle methocel 0.5%) | | 173 | 387 |
| | Example 4 | 0.1 | 157** | 382 |
| | | 1 | 153** | 380 |
| | Example 5 | 0.1 | 154** | 390 |
| | Example 23 | 1 | 159** | 370 |
| | Example 27 | 1 | 156** | 390 |
| | Example 25 | 0.1 | 164 | 395 |
| | Example 26 | 1 | 164 | 374 |
| | Example 6 | 1 | 166 | 392 |
| B | (vehicle methocel 0.5%) | | 171 | 377 |
| | Example 12 | 10 | 156** | 380 |

Milan Hypertensive Rats (MHS)

Milan hypertensive rats is a rat model of genetic hypertension sustained by α-adducin mutation and increased circulating levels of endogenous ouabain (Ferrari P., et al., Hypertension: Pathophysiology, Diagnosis and Management, (Volume 1). Laragh J H and Brenner B M (Eds.), Raven Press Publishers, New York, USA, 1261-1279, (1995).

The compounds were administered by oral gavage (10 μg/kg/day) for six weeks. The systolic blood pressure and heart rate after a six week treatment are reported in table 3 underneath.

TABLE 3

| Experiments | Compounds | SBP, mmHg | HR, beats/min |
|---|---|---|---|
| A | (vehicle methocel 0.5%) | 169 | 348 |
| | Example 12 | 161* | 347 |
| B | (vehicle methocel 0.5%) | 164 | 363 |
| | Example 27 | 156* | 367 |
| | Example 5 | 155* | 367 |

*$p < 0.05$ vs control

Compounds of examples 12 and 27 significantly reduced SBP in MHS rats at the dose tested meanwhile example 4 was not effective on SBP. None of the derivatives affected HR in MHS.

The effect of the compound of example 4 on urinary protein excretion was investigated. Increased levels of circulating endogenous ouabain not only associate with hypertension but also may affect renal function and increase the risk of renal failure and proteinuria (Stella P., et al., *J. Int. Med.*, 2008, 263, 274) which represent major organ complications associated to hypertension.

OHR rat model showed an increased urinary protein excretion and plasma creatinine concentration coupled to reduced creatinine clearance as compared with saline infused control rats.

OHR rats were orally treated with the compound of example 4 at 0.1 μg/kg/day for 6 weeks. At the end of the treatment, rats were allocated in single metabolic cages for 24 h urine collection.

Proteinuria and urinary creatinine were measured by commercial kits (Sentinel). Rats were sacrificed and blood was collected for plasma creatinine measurement. The data are reported in table 4 underneath.

TABLE 4

| Experiment | Proteinuria mg/24 hr | Urinary creatinine mg/24 h | Plasma creatinine mg/dl | Creatinine clearance ml/min |
|---|---|---|---|---|
| Controls (saline infused rats) | 35.6 | 36.1 | 3.1 | 0.81 |
| OHR vehicle (methocel 0.5%) | 51.6 ± 5* | 33.7 | 3.51* | 0.66* |
| OHR vehicle + example 4 | 42** | 35.6 | 3.59 | 0.69 |

*$p < 0.05$ vs control;
**$p < 0.05$ vs non-treated OHR

Example 4 at 0.1 μg/kg/day significantly reduced the urinary protein excretion in OHR rats.

The invention claimed is:

1. A compound having the general formula I

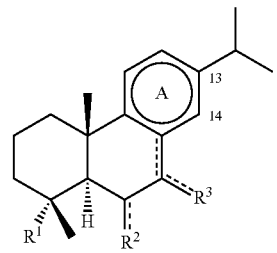

wherein:

$R^1$ is —CH=NOR$^4$ with the meaning of iminoxy, —CH$_2$NHOR$^4$, —CH$_2$XR$^5$, —CH=CHR$^6$, —CH=NR$^7$, or NH$_2$—(C$_3$-C$_6$)alkyl-;

$R^7$ is guanidino;

$R^6$ is NH$_2$—(C$_1$-C$_6$)alkyl-;

$R^5$ is NH$_2$—(C$_1$-C$_6$)alkyl-;

$R^4$ is NH$_2$—(C$_1$-C$_6$)alkyl-, piperidinyl, hydroxy-(C$_1$-C$_6$)-alkyl-, hydroxy-(C$_1$-C$_6$)-alkyloxy-(C$_1$-C$_6$)-alkyl-, or carboxy-(C$_1$-C$_6$)-alkyl-;

X is O or S;

the endocyclic symbol === represents a single or a double bond and when it represents a double bond the symbol === linking R$^3$ to the carbocycle represents a single bond and the carbocycle ring A is partially unsaturated possessing only one double bond between carbon atoms 13-14;

the symbol === linking R$^2$ to the carbocycle represents a single or a double bond; R$^2$ is H or hydroxyl when the symbol === linking R$^2$ to the carbocycle represents a single bond; or R$^2$ is O or N~OR$^8$ when the symbol === linking R$^2$ to the carbocycle represents a double bond with the meaning of carbonyl or oxime respectively;

$R^8$ is H or $(C_1-C_6)$alkyl;

the symbol ═ linking $R^3$ to the carbocycle represents a single or a double bond; $R^3$ is H when the symbol ═ linking $R^3$ to the carbocycle represents a single bond; or $R^3$ is O or N~$OR^8$ when the symbol ═ linking $R^3$ to the carbocycle represents a double bond with the meaning of carbonyl or oxime respectively;

carbocycle ring A is aromatic or partially unsaturated possessing only one double bond between carbon atoms 13-14;

their optically active forms such as enantiomers, diastereomers, their racemate forms, and pharmaceutically acceptable salts thereof.

2. The compound according to claim 1, wherein $R^1$ represents —CH═$NOR^4$.

3. The compound according to claim 1, wherein $R^4$ is $NH_2$—$(C_1-C_6)$alkyl.

4. A medicament comprising an effective amount of a compound according to claim 1.

5. A pharmaceutical composition comprising a compound according to claim 1 together with a pharmaceutically acceptable excipient.

6. Process for synthesizing compounds of claim 1, wherein the symbol $R^1$ is —CH═$NOR^4$ with the meaning of iminoxy; carbocycle ring A is aromatic or partially unsaturated and $R^2$ and $R^3$ are as defined above, comprising reacting a compound of Formula II,

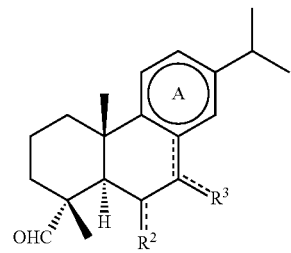
Formula (II)

wherein carbocycle ring A is aromatic or partially unsaturated and $R^2$ and $R^3$ are as defined above, with a compound of formula (III)

$R^4ONH_2 \cdot x HCl$ (formula (III))

wherein $R^4$ is as defined above, and x is an integer between 0 and 3; in pyridine at room temperature.

7. The medicament according to claim 4, wherein said effective amount comprises from 0.1 to 50% by weight.

8. The medicament according to claim 4, wherein said effective amount comprises from 1 to 40% by weight.

* * * * *